United States Patent
Burkholz et al.

(10) Patent No.: US 9,314,201 B2
(45) Date of Patent: *Apr. 19, 2016

(54) REMOVABLE FLASH CHAMBER

(71) Applicant: Becton, Dickinson and Company, Franklin Lakes, NJ (US)

(72) Inventors: Jonathan Karl Burkholz, Salt Lake City, UT (US); Minh Quang Hoang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/065,727

(22) Filed: Oct. 29, 2013

(65) Prior Publication Data

US 2014/0052021 A1   Feb. 20, 2014

Related U.S. Application Data

(62) Division of application No. 13/181,265, filed on Jul. 12, 2011, now Pat. No. 8,597,252.

(60) Provisional application No. 61/364,535, filed on Jul. 15, 2010.

(51) Int. Cl.
  *A61M 5/178* (2006.01)
  *A61M 5/32* (2006.01)
  (Continued)

(52) U.S. Cl.
  CPC ............. *A61B 5/1535* (2013.01); *A61B 5/1422* (2013.01); *A61B 5/15003* (2013.01); *A61B 5/15074* (2013.01); *A61B 5/150213* (2013.01); *A61B 5/150274* (2013.01); *A61B 5/150389* (2013.01); *A61B 5/150519* (2013.01); *A61B 5/150641* (2013.01); *A61B 5/150916* (2013.01); *A61B 5/150992* (2013.01);
  (Continued)

(58) Field of Classification Search
  CPC .. A61B 5/1535; A61B 5/1545; A61B 5/1422; A61M 25/0693
  USPC .......... 604/164.01–164.11, 168.01, 122, 126; 600/573, 576–587
  See application file for complete search history.

(56) References Cited

U.S. PATENT DOCUMENTS 3,859,998 A   1/1975   Thomas et al.
4,003,403 A   1/1977   Nehring
(Continued)

FOREIGN PATENT DOCUMENTS

EP   0 812 601 A2   12/1997
EP   1 884 257 A1   2/2008
(Continued)

*Primary Examiner* — Matthew F DeSanto
(74) *Attorney, Agent, or Firm* — Jeanne Lukasavage; Craig Metcalf; Kirton McConkie

(57) ABSTRACT

A needle hub and catheter assembly are disclosed herein. The needle hub includes an introducer needle having a lumen extending therethrough. A needle hub is coupled to a proximal end of the introducer needle. A flash chamber is removably coupled to the needle hub or the introducer needle. An interior of the flash chamber is in fluid communication with the lumen of the introducer needle when the flash chamber is coupled to the needle hub or the introducer needle. As such, the flash chamber can collect a sample of blood that can be accessed when the flash chamber is removed. In some instances, the blood can also be dispensed from the flash chamber into a test strip or other testing device.

19 Claims, 9 Drawing Sheets

(51) Int. Cl.
  *A61B 5/153* (2006.01)
  *A61B 5/15* (2006.01)
  *A61M 25/06* (2006.01)

(52) U.S. Cl.
  CPC ...... *A61M 25/0631* (2013.01); *A61M 25/0693* (2013.01); *Y10T 29/49826* (2015.01)

(56) References Cited

U.S. PATENT DOCUMENTS

| | | | |
|---|---|---|---|
| 4,172,448 A * | 10/1979 | Brush | 600/579 |
| 4,193,399 A | 3/1980 | Robinson | |
| 4,200,096 A | 4/1980 | Charvin | |
| 4,266,559 A * | 5/1981 | Akhavi | 600/579 |
| 4,269,186 A | 5/1981 | Loveless et al. | |
| 4,682,980 A | 7/1987 | Suzuki | |
| 4,703,761 A * | 11/1987 | Rathbone et al. | 600/576 |
| 4,765,588 A | 8/1988 | Atkinson | |
| 4,772,264 A | 9/1988 | Cragg | |
| 4,917,671 A | 4/1990 | Chang | |
| 4,935,010 A | 6/1990 | Cox et al. | |
| 5,032,116 A | 7/1991 | Peterson et al. | |
| 5,215,529 A | 6/1993 | Fields et al. | |
| 5,226,883 A | 7/1993 | Katsaros et al. | |
| 5,242,411 A | 9/1993 | Yamamoto et al. | |
| 5,290,246 A | 3/1994 | Yamamoto et al. | |
| 5,368,029 A | 11/1994 | Holcombe et al. | |
| 5,542,932 A | 8/1996 | Daugherty | |
| 5,730,123 A | 3/1998 | Lorenzen et al. | |
| 5,800,399 A * | 9/1998 | Bogert et al. | 604/164.11 |
| 5,947,932 A | 9/1999 | Desecki et al. | |
| 6,872,193 B2 * | 3/2005 | Shaw et al. | 604/164.07 |
| 8,066,670 B2 | 11/2011 | Cluff et al. | |
| 8,070,725 B2 | 12/2011 | Christensen | |
| 8,597,252 B2 * | 12/2013 | Burkholz et al. | 604/168.01 |
| 2004/0181192 A1 | 9/2004 | Cuppy | |
| 2005/0273019 A1 | 12/2005 | Conway et al. | |
| 2007/0043334 A1 | 2/2007 | Guala | |
| 2007/0191777 A1 * | 8/2007 | King | 604/164.08 |
| 2008/0255473 A1 | 10/2008 | Dalebout et al. | |
| 2008/0287876 A1 * | 11/2008 | Shue et al. | 604/164.08 |
| 2008/0287906 A1 | 11/2008 | Burkholz et al. | |
| 2009/0099431 A1 | 4/2009 | Dalebout et al. | |
| 2012/0016213 A1 | 1/2012 | Burkholz | |
| 2012/0016265 A1 | 1/2012 | Peterson et al. | |

FOREIGN PATENT DOCUMENTS

| | | |
|---|---|---|
| JP | 2007-029732 A | 2/2007 |
| WO | 01/12254 A1 | 2/2001 |
| WO | 2004/098685 A1 | 11/2004 |
| WO | 2008/058132 A2 | 5/2008 |
| WO | 2008/058133 A2 | 5/2008 |

* cited by examiner

REMOVABLE FLASH CHAMBER

RELATED APPLICATIONS

This application is a divisional of U.S. patent application Ser. No. 13/181,265, filed Jul. 12, 2011, titled REMOVABLE FLASH CHAMBER, which claims the benefit of U.S. Provisional Application No. 61/364,535 filed Jul. 15, 2010, titled CATHETER WITH REMOVABLY ATTACHED VENTED FLASH CHAMBER FOR BLOOD SAMPLING AND POINT OF CARE DIAGNOSTIC BLOOD TESTING, and are incorporated herein by reference.

BACKGROUND

The present disclosure relates to venting air and blood sampling with vascular access devices. Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples are analyzed via one or more blood test levels.

Blood tests determine the physiological and biochemical states of the patient, such as disease, mineral content, drug effectiveness, and organ function. Blood tests may be performed in a laboratory, a distance away from the location of the patient, or performed at the point of care, near the location of the patient. One example of point of care blood testing is the routine testing of a patient's blood glucose levels. This involves the extraction of blood via a finger stick and the mechanical collection of blood into a diagnostic cartridge. Thereafter the diagnostic cartridge analyzes the blood sample and provides the clinician a reading of the patient's blood glucose level. Other devices are available which analyze blood gas electrolyte levels, lithium levels, ionized calcium levels. Furthermore, some point-of-care devices identify markers for acute coronary syndrome (ACS) and deep vein thrombosis/pulmonary embolism (DVT/PE).

Blood testing is frequently necessary prior to surgery or other medical procedures. For example, there are indications that diabetes contributes to an increase risk of Surgical Site Infection (SSI). Accordingly some guidelines suggest that diabetes is one characteristic that may influence the development of SSI. As such, preoperative blood glucose control is deemed a possible SSI risk reduction measure. Testing of creatine-based estimated glomerular filtration rate (GFR) can also be useful prior to some medical procedures. In February 2002, The National Kidney Foundation published that GFR is the best overall indicator of kidney function. The demonstration of normal kidney function may be important prior to a patient obtaining a contrast enhanced CT scan, which can have significant impact on the kidneys. Despite these needs, blood diagnosis is typically done at remote labs, which do not produce immediate results.

Furthermore, despite the rapid advancement in point of care testing and diagnostics, blood sampling techniques have remained relatively unchanged. Blood samples are frequently drawn using hypodermic needles or vacuum tubes coupled to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Furthermore, each device required adds time and cost to the testing process. Accordingly, there is a need for more efficient blood sampling and testing devices and methods.

SUMMARY

The present invention has been developed in response to problems and needs in the art that have not yet been fully resolved by currently available blood sampling devices and methods. Thus, these devices and methods are developed to efficiently collect a blood sample from a flash chamber that is removably coupled to the proximal end of an introducer needle. Since blood is already collected in this chamber, the use of this blood can avoid the need for a separate blood sampling procedures and devices, which can decrease the cost and time of blood diagnosis. Once removed, blood can be dispensed from the flash chamber into a point-of-care diagnostic device, for prompt test results, which can enable time-sensitive health information, such as the risk of diabetes or impaired kidney function to be more quickly and easily acquired. Furthermore, the flash chamber can be sized to accommodate the desired blood sample. As such, the flash chamber can be enlarged, which increases the flashback visualization period.

In one aspect of the invention, a needle hub comprises: an introducer needle having a lumen extending therethrough; a needle hub coupled to a proximal end of the introducer needle; and a flash chamber removably coupled to the needle hub, an interior of the flash chamber being in fluid communication with the lumen of the introducer needle when the flash chamber is coupled to the needle hub.

Implementation may include one or more of the following features. A portion of the flash chamber can be compressible. The flash chamber can comprise: a chamber body defining an internal cavity; and an air permeable membrane coupled to the chamber body and in fluid communication with the internal cavity. The internal cavity of the chamber body of the flash chamber can have in an internal volume between about 0.1 mL to about 10 mL. The flash chamber can be press fit into the needle hub or introducer needle. The flash chamber can be screwed onto the needle hub. The flash chamber can be selectively coupled to the needle hub or the introducer needle via a keyed connection. The flash chamber can be selectively coupled to the needle hub or the introducer needle via a breakable connection. The flash chamber can be a breakable ampoule.

In another aspect of the invention, a catheter assembly comprises: an introducer needle having a lumen extending therethrough; a needle hub coupled to a proximal end of the introducer needle; a flash chamber selectively coupled to the needle hub or the introducer needle, an interior of the flash chamber being in fluid communication with the lumen of the introducer needle when the flash chamber is coupled to the needle hub, the flash chamber having an air permeable membrane and a distal connector portion; the chamber body defining an internal cavity, the chamber body having at least a compressible portion that decreases the internal volume of the internal cavity when compressed; the air permeable membrane coupled to the chamber body and in fluid communication with the internal cavity; and the distal connector portion of the chamber body for selectively coupling to the needle hub.

Implementation may include one or more of the following features. At least a portion of the flash chamber can be compressible. The flash chamber can have an internal volume between about 0.1 mL to about 10 mL. The flash chamber can be press fit into the needle hub or introducer needle. The flash chamber can be screwed onto the needle hub. The flash chamber can be selectively coupled to the needle hub or the introducer needle via a breakable connection, the breakable connection including at least one scored line and a stress riser. The flash chamber is a breakable ampoule.

In another aspect of the invention, a method for providing a removable flash chamber of a catheter assembly, the method comprising: providing a catheter assembly having a needle hub, the needle hub having an introducer needle coupled thereto; providing an introducer needle coupled to the needle hub, the introducer needle having a lumen extending therethrough; and providing a flash chamber removably coupled to the needle hub, an interior of the flash chamber being in fluid communication with the lumen of the introducer needle when the flash chamber is coupled to the needle hub.

Implementation may include one or more of the following features. The method may further comprise providing at least a single compressible portion of the flash chamber for selectively ejecting blood within the flash chamber from therefrom. The method may further comprise providing an inner cavity within a body of the flash chamber having an internal volume about 0.1 mL to 10 mL. The flash chamber can have a distal connector portion, the distal connector portion having at least one of a press fit connector, screw threads, a keyed connection, and a breakable connection.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
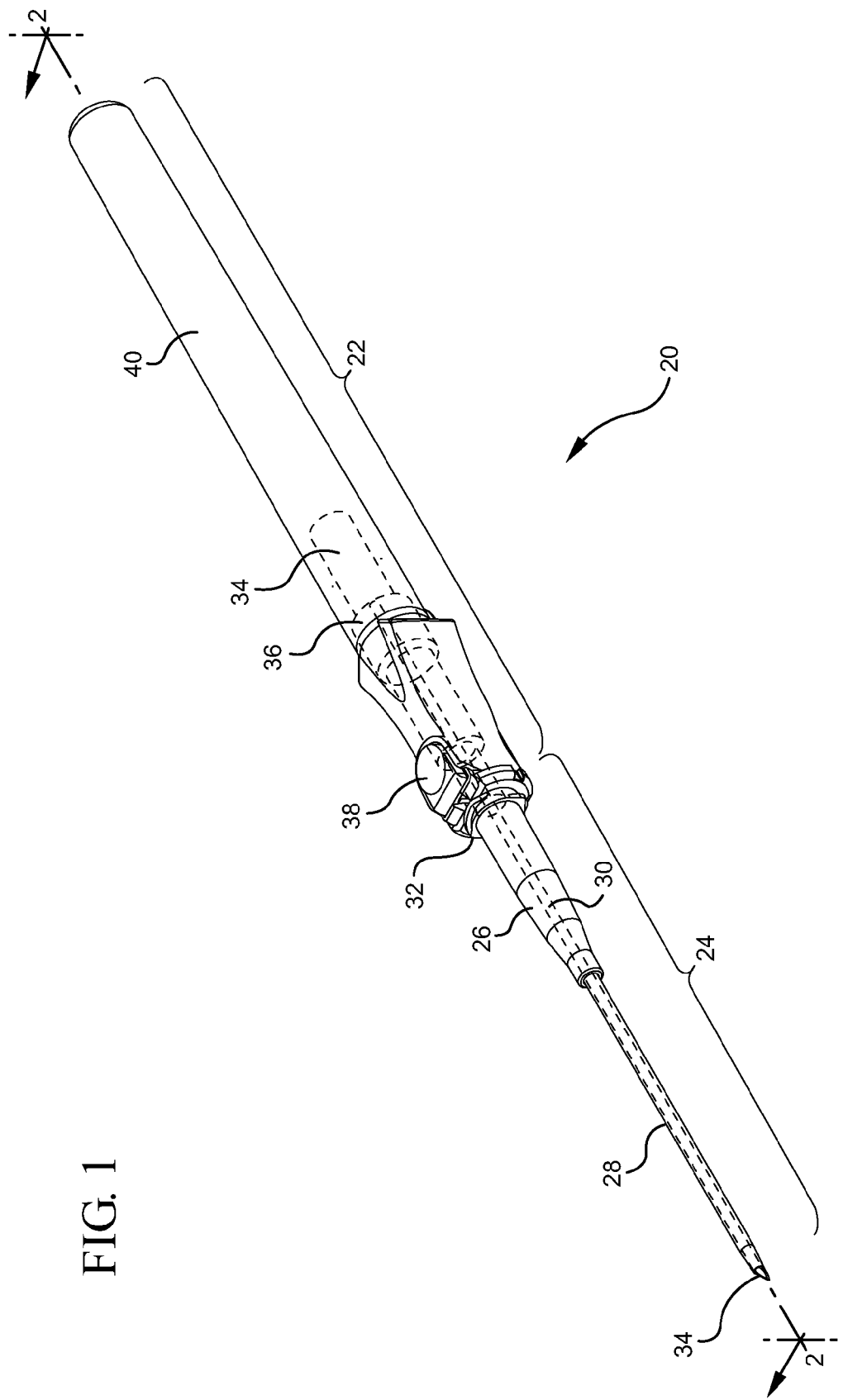
FIG. 1 illustrates a perspective view of a catheter assembly with a removable flash chamber, according to some embodiments.

Reference will now be made to FIG. 1, which illustrates a catheter assembly 20 that can be used to access the vascular system of a patient, such as the BD Insyte™ Autoguard™ from Beckton, Dickinson and Company, Inc. (as shown), the BD Protect IV™ also from Beckton, Dickinson and Company, Inc., and the Medikit Z5 from Medikit Company Inc. The catheter assembly 20 can include various other configurations. The catheter assembly 20 generally includes a catheter adapter 24 and a needle assembly 22. The catheter adapter 24 is inserted into a patient to establish fluid communication with the patient's vasculature, and may be used to infuse fluids therethrough. The needle assembly 22 includes an introducer needle 30 that is used to assist the catheter assembly 24 to be accurately placed into the vasculature of the patient. After the catheter assembly 24 is properly placed, the needle assembly 22 is removed and uncoupled from the catheter assembly 24.

The needle assembly 22 includes a generally rigid introducer needle 30 that provides structural support to the flexible or semi-flexible catheter 28 of the catheter assembly 24. In a pre-use position, the introducer needle 30 is inserted through the catheter 28, as shown. During infusion or other such procedures the introducer needle 30 and catheter 28 are inserted through the skin of a patient and advanced into the vasculature of a patient. Once the catheter 28 is properly placed, the introducer needle 30 is removed from the catheter 28.

As shown in FIG. 1, the catheter adapter 24 includes a catheter hub 26 that is coupled to a catheter 28 that extends distally from the distal end of the catheter hub 26. The catheter hub 26 includes an inner lumen that extends therethrough and provides fluid communication to an inner lumen of the catheter 28. In some configurations, the catheter hub 26 also includes a proximal connector 32, such as a threaded luer connector, that can connect to a needle assembly 22 or other vascular access device.

The needle assembly 22 includes an introducer needle 30 that extends through the catheter assembly 20 in a pre-insertion state. The introducer needle 30 is coupled to a needle hub 36 at its proximal end. In some embodiments, as shown, the needle hub 36 is disposed within a safety barrel 40 that shields the introducer needle 30 after it is withdrawn from the patient and out of the catheter adapter 24. In the illustrated embodiment, the introducer needle 30 is withdrawn, via a spring force, from the catheter adapter 24 when a user presses a button 38 of the needle assembly 22. The button 38 releases a fastener that holds the introducer needle 30 in place, permitting it to be withdrawn proximally through the catheter 28 and catheter hub 26 into the safety barrel 40.

With continued reference to FIG. 1, in some embodiments, a flash chamber (also known as "flashback chamber") 34 is coupled to the needle hub 36 or directly to the proximal end of the introducer needle 30. The flash chamber 34 can receive blood therein from the introducer needle 30. In some configurations, the flash chamber 34 is transparent or semi-transparent such that a user can view blood flowing into the flash chamber 34 from the introducer needle 30.

In some catheter placement procedures, flashback occurs when blood from within the vasculature of a patient enters into the catheter 28 and/or introducer needle 30 of the catheter assembly 20. In some instances, the catheter 28 is transparent or semi-transparent such that the clinician can recognize blood flowing through the catheter 28 after the introducer needle 30 has entered the patient's vascular. To provide an extended flashback period that may enable a clinician to verify that the catheter 28 has entered and remains properly placed. In some embodiments, the catheter hub 26 and/or the needle assembly 22 can include a flash chamber 34. A flash chamber 34 of the needle assembly 22 can be in fluid communication with the introducer needle 30 so that blood flowing through the introducer needle 30 enters into the flash chamber 34. The size of the flash chamber 34 can be varied so that the length of time required to fill the chamber provides the clinician adequate time to properly position the catheter 28. As mentioned, once the catheter 28 is properly placed, the introducer needle 30 can be withdrawn from the catheter 28.

After the needle assembly 22 is uncoupled from the catheter adapter 24, the sample of blood within the flash chamber 34 can be use for diagnosis. In some embodiments, the flash chamber 34 can be selectively uncoupled from the needle assembly 22 so that the blood therein can be accessed and tested. Thus, in some embodiments, there is a means for extracting the blood from the flash chamber 34. This means can include compressing at least a portion of the flash chamber 34 to dispense blood therefrom. This means can also include breaking the flash chamber 34, sucking or wicking blood from the flash chamber 34, or otherwise removing the blood therefrom.

In some embodiments, the flash chamber 34 extends through a proximal opening 60 in the safety barrel 40 after the needle is withdrawn from the catheter adapter 24. Thus, the flash chamber 34 can be larger, with an increased internal volume, than it could be without a proximal opening 60. In some configurations, the flash chamber 34 has in an internal volume between about 0.1 mL to 10 mL. In other configurations, the flash chamber 34 has in an internal volume between about 0.5 mL to 7 mL. In other configurations, the flash chamber 34 has in an internal volume between about 1 mL to 3 mL. In other configurations, the flash chamber 34 has in an internal volume greater or less than the listed volumes. The larger internal volume of the flash chamber 34 can provide longer flashback indication periods. As such, a clinician can have more time to place and ensure proper placement of the catheter 28.

Figure 2:
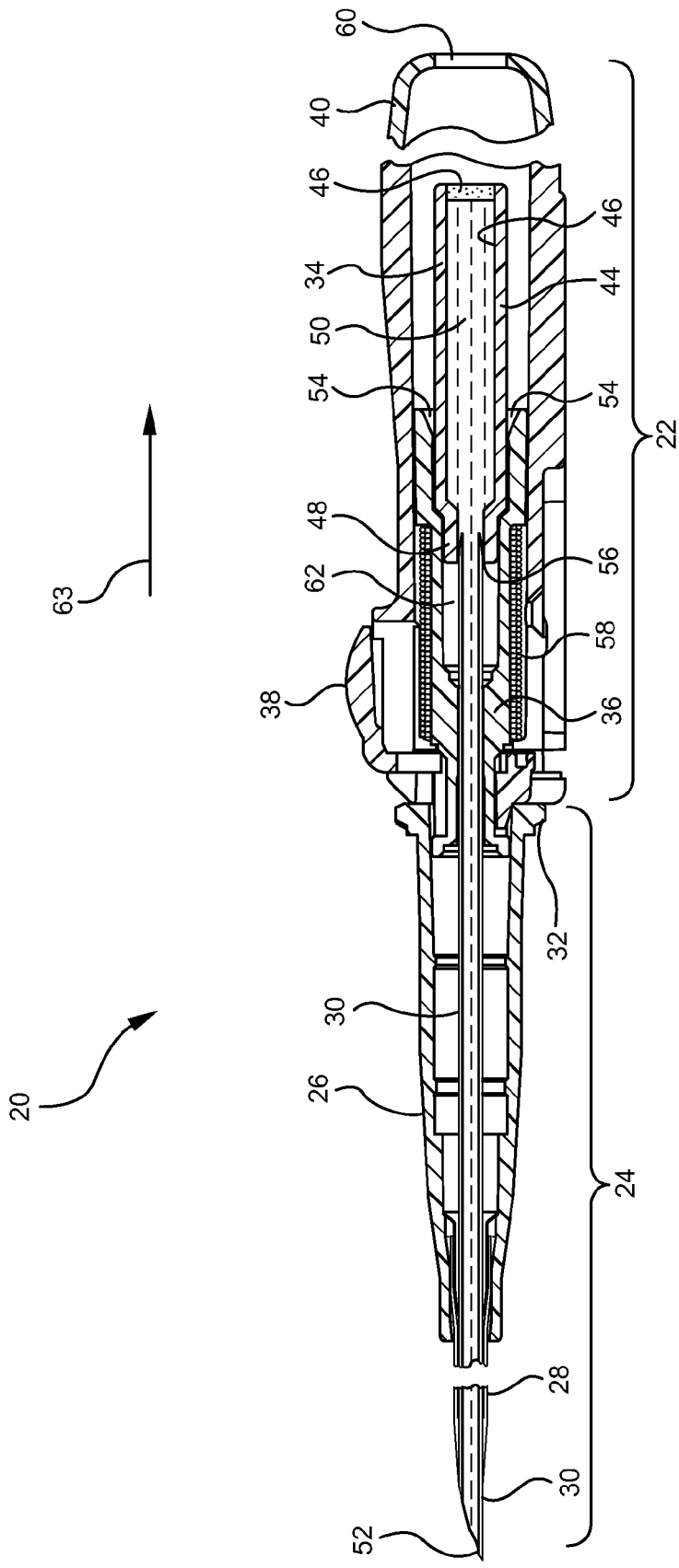
FIG. 2 illustrates a cross-section view of a catheter assembly of FIG. 1 taken along line 2-2, according to some embodiments.

Reference will now be made to FIG. 2, which depicts a cross section of the catheter assembly 20 of FIG. 1 taken along line 2-2. This figure depicts at least some of the inner components of the catheter adapter 24 and needle assembly 22. For simplicity, the catheter hub 26 is depicted as having few features or components therein. However, it will be understood that the catheter hub 26 can include various known components and features, such as a valve, blood control valve, inner ridges, or other known elements.

As shown in FIG. 2, in some embodiments, the needle assembly 22 includes a needle hub 36 coupled to an introducer needle 30, a spring 58, and a removable flash chamber 34. These components can be at least partially disposed within a safety barrel 40 that prevents blood and needle exposure after the introducer needle 30 is drawn into the safety barrel 40. A cross section of the button 38 and its related components shows how the button 38, when depressed, disengages the needle hub 36, which is then moved proximally 62 under the force of the spring 58. The spring 58 is positioned between the safety barrel 40 and the needle hub 36, so that when the button 38 is depressed it releases its mechanical energy, uncompresses, and forces the needle hub 36 proximally 62. In some instances, the spring 58 is a compression spring that stored energy when compressed. In some configurations, the flash chamber 34 is disposed on the proximal end of the needle hub 36, and the flash chamber 34 extends at least partially out of a proximal opening 60 in the safety barrel 40 as it moves to the proximal end of the safety barrel 40. The tip of the introducer needle 30 can be drawn into the safety barrel 40 as the needle hub 36 is forced proximally 63. This movement draws the introducer needle 30 and its tip into a shielded position, within the covering and the containment of the safety barrel 40, which can serve as a shield between the introducer needle 30 and the clinician to prevent needle stick injuries and blood contamination.

Figure 3:
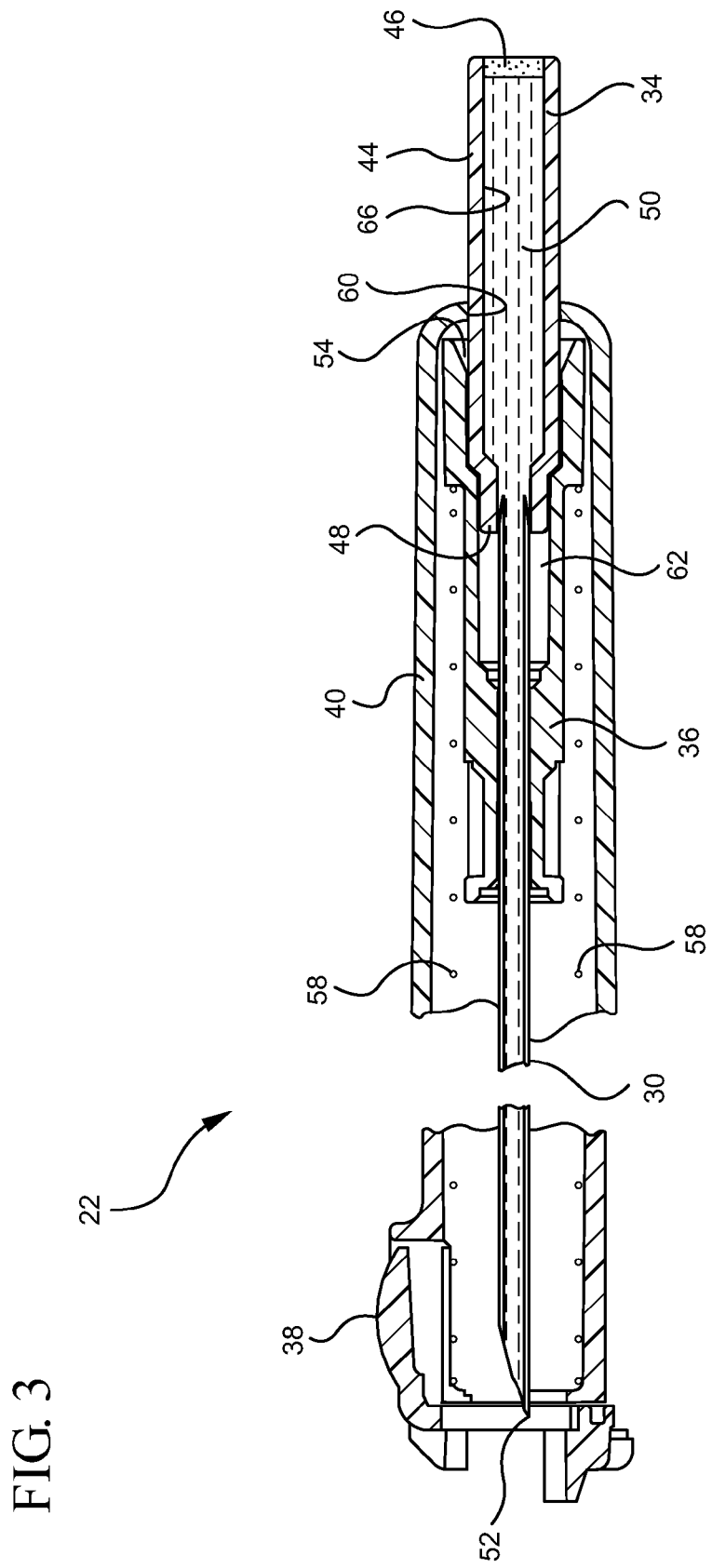
FIG. 3 illustrates a cross-section view of a catheter assembly with a removable flash chamber after the introducer needle has been withdrawn from the catheter, according to some embodiments.
Figure 6:
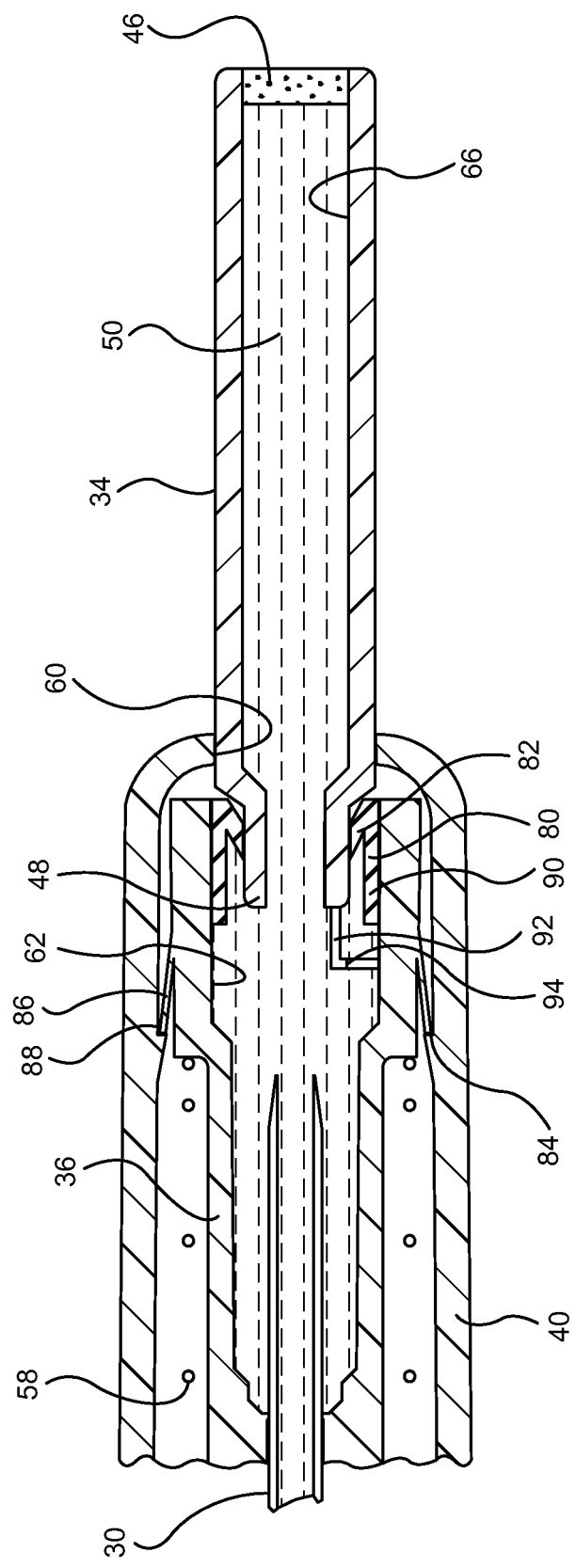
FIG. 6 illustrates a cross-section view of a proximal portion of a catheter assembly with a removable flash chamber, according to some embodiments.

In some instances, in the shielded position as shown in FIG. 3, the introducer needle 30 is safely contained within the safety barrel 40 while the flash chamber 34 extends at least partly out of a proximal opening 60 of the safety barrel 40. In some embodiments, the proximal opening 60 is shaped and sized to conform quite closely to the outer geometry of the flash chamber 34 so as to minimize any spacing therebetween that might otherwise provide room for blood flow of blood within the safety barrel 40. In the shielded position, a proximal portion of the flash chamber 34 can be accessed by a clinician and selectively uncoupled from the needle hub 36. Depending on the type of coupling between the flash chamber 34 and the needle hub 36 or introducer needle 30, the clinician will pull and/or twist, or otherwise manipulate the flash chamber 34 to uncouple it from the needle hub 36. In some configurations, the flash chamber 34 is directly coupled to the needle hub 36 and the introducer needle 30, as shown in FIG. 2. In some configurations, the flash chamber 34 is indirectly coupled to the needle hub 36 and directly coupled to the introducer needle 30, which is directly coupled to the needle hub 36. In other configurations, the flash chamber 34 is indirectly coupled to the needle 30 and directly coupled to the needle hub 36, which is directly coupled to the introducer needle 30, as shown in FIG. 6.

Referring again to FIG. 2, in some embodiments, the flash chamber 34 is removably or selectively coupled to the needle hub 36. This removable coupling can have various configurations, such as a press-fit coupling, a threaded screw-on coupling, a keyed connection, a breakable connection, and other various types of removable couplings. As shown, the flash chamber 34 is press fit within an inner bore 62 of the needle hub 36. Also shown, the introducer needle 30 is press fit within the flash chamber 34. In some embodiments, only one of these press-fit couplings is used, rather than both. In a press-fit coupling, the inner geometry of the inner bore 62 approximates and may be approximately equal to or slightly smaller than the outer geometry of the chamber body 44 of the flash chamber 34. Additionally or alternatively, the inner surface of the inner bore 62 can include one or more inward protrusions 54 that press against the outer surface of the chamber body 44 to provide pressure between these components. In other embodiments, the outer surface of the chamber body of the flash chamber 34 includes one or more outward protrusions that press against the inner surface of the inner bore 62 to provide pressure between these components.

Figure 8:
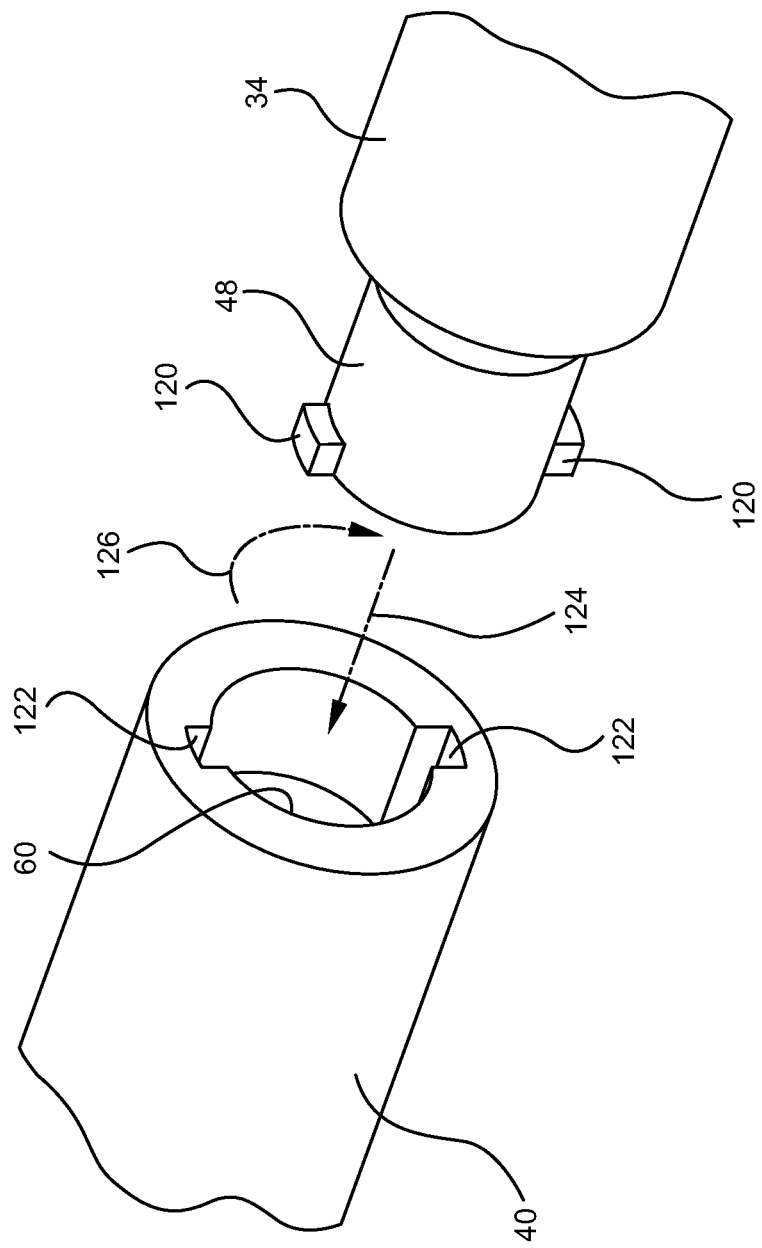
FIG. 8 illustrates a perspective view of a keyed connection between a flash chamber and a needle hub or safety barrel, according to some embodiments.

In some embodiments, flash chamber 34 includes a distal connector portion 48 of the chamber body 44 for selectively coupling to the needle hub 36. As shown in FIG. 2, this distal connector portion 48 includes the distal portion of the chamber body 44, which has an outer geometry that is press fit into the needle hub 36 and over the proximal end of the introducer needle 30. In other embodiments, the distal connector portion 48 includes a threaded member used to screw the flash chamber 34 into the needle hub 36. In some embodiments, the distal connector portion 48 includes a keyed connection that mates with a keyed portion of the needle hub 36, as shown in FIG. 8. In some embodiments, the distal connector portion 48 includes a breakable connection having, for example, a scored line and/or a stress riser.

In some embodiments, the flash chamber 34 includes a membrane 46 that is air permeable, through which air from within the introducer needle 30 passes. In some embodiments, the membrane 46 is hydrophobic so that it does not permit blood to pass through it. In such embodiments, blood 50 entering the introducer needle 30 forces air out the membrane 46 as it enters the introducer needle 30 and fills the introducer needle 30 and the flash chamber 34 to the membrane 46. At this point, blood 50 ceases to flow into the introducer needle 30.

In some embodiments, the membrane 46 is both air permeable and hydrophobic, to permit air, but not blood 50 to pass therethrough. In other embodiments, the membrane 46 is hydrophilic. The membrane 46 can include various materials and components that provide these properties. For example, in some embodiments, the membrane 46 includes glass, polyethylene terephthalate (PET), a microfiber material, and/or other synthetic material made of high-density polyethylene fibers, such as TYVEK® material from DuPont. Other such materials and components can also be used as a layer of the membrane 46 or as the entire membrane 46 to enable the membrane 46 to be hydrophobic, hydrophilic, and/or air permeable, according to some configurations.

In some embodiments, the flash chamber 34 is configured to retain blood 50 as it is withdrawn from the needle hub 36 to prevent blood spills and blood contamination. Thus, in some configurations, a distal opening 56 of the flash chamber 34 is shaped and sized to retain blood 50. Blood retention within the internal cavity 66 is governed, at least in part, by the inner perimeter of the distal opening 56, the surface tension of blood 50, and the force on the blood 50 to flow out of the distal opening 56. Accordingly, the inner perimeter of the distal opening 56 can be designed so that blood 50 is retained within the internal cavity 66 when the force of the blood 50 to flow out of the distal opening 56 is within a certain range, but permit at least some blood to flow out when the pressure on the blood 50 exceeds this range.

For example, in some embodiments, when the distal opening 56 is circular, an inner perimeter of less than or equal to approximately 2.0 mm, and a diameter of less than or equal to approximately 0.6 mm, permits the retention of blood 50 within the internal cavity 66 against approximately the force of gravity. When the force on the blood 50 is greater than the force of gravity some blood 50 can flow out of the distal opening 56. Similarly, a circular distal opening 56 with a diameter of about 0.3 mm may retain blood 50 therein against forces stronger than gravity, such as bumping, jarring, and movement of the filled flash chamber 34. When the distal opening 56 has a very small inner perimeter, the force required to expel blood 50 will be very large.

In some embodiments, the distal opening 56 has a inner perimeter greater than or equal to about 0.3 mm, which when the distal opening 56 is a circular opening, corresponds to a diameter of about 0.1 mm. Thus, in some configurations, the distal opening 56 has an inner perimeter between about 0.3 mm to about 2.0 mm. In some configurations, the distal opening 56 is approximately circular and has a diameter between about 0.1 mm to about 0.6 mm. In other embodiments, the distal lumen opening 58 is non-circular.

Reference will now be made to FIG. 3, which depicts the needle assembly 22 in the shielded position, with the spring 58 released to a decompressed state, which has forced the needle hub 36 to the proximal end of the safety barrel 40 and the flash chamber 34 at least partially out of the proximal opening 60 of the safety barrel 40. The internal cavity 66 of the flash chamber 34 is filled at least partially with blood 50. In this shielded position, the proximal portion of the chamber body 44 can be gripped and selectively decoupled from the needle hub 36. In this manner, the blood 50 sample within the flash chamber 34 can be used for diagnosis.

Figure 4:
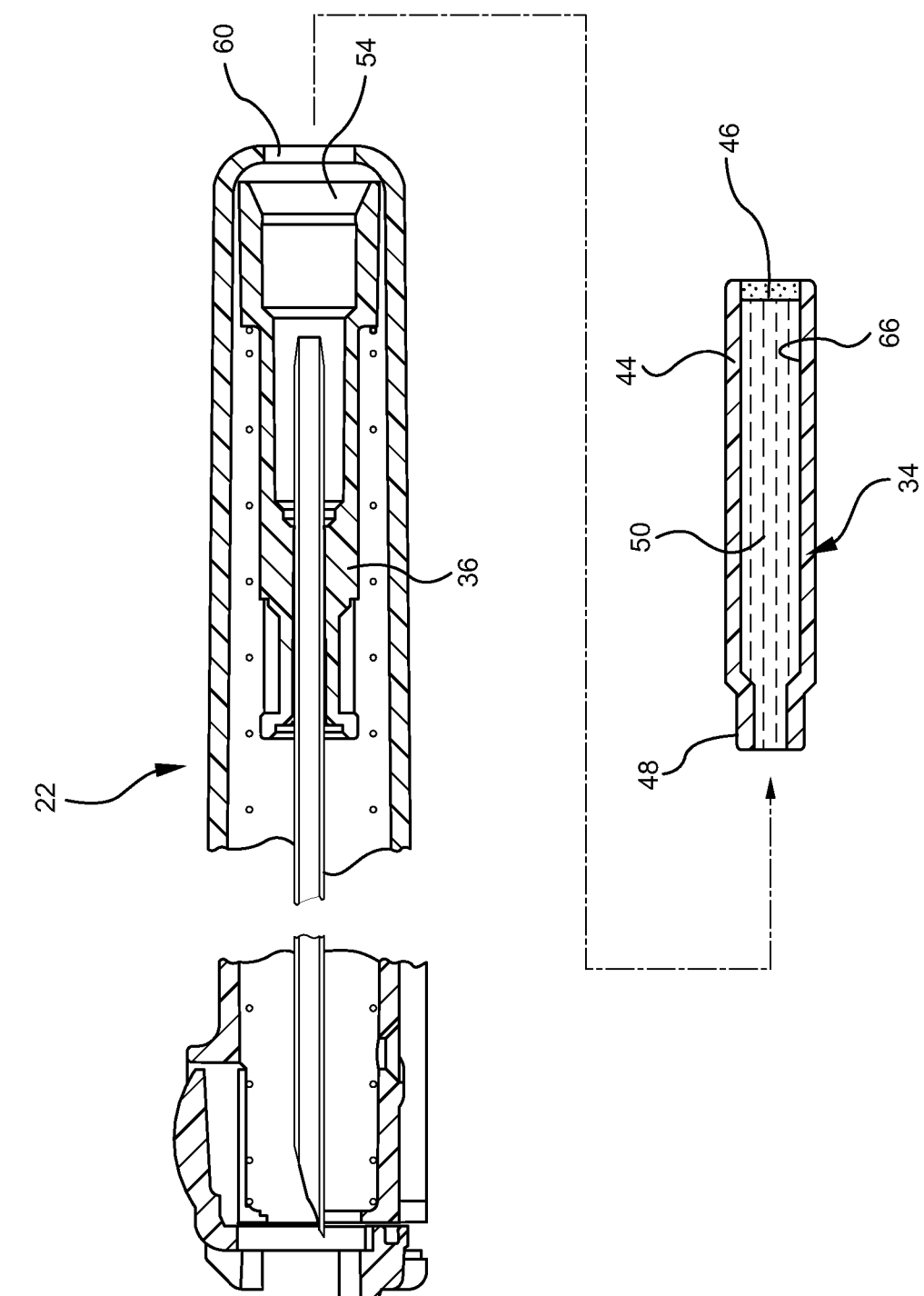
FIG. 4 illustrates a perspective view of a catheter assembly with a removable flash chamber that has been removed therefrom, according to some embodiments.

As shown in FIG. 4, flash chamber 34 is decoupled from the needle assembly 22. This flash chamber 34 can now be used as a storage vial of blood 50 as it is transported to a testing facility. Additionally, the blood 50 sample within the flash chamber 34 can be immediately used for point-of-care blood diagnostic testing.

Figure 5:
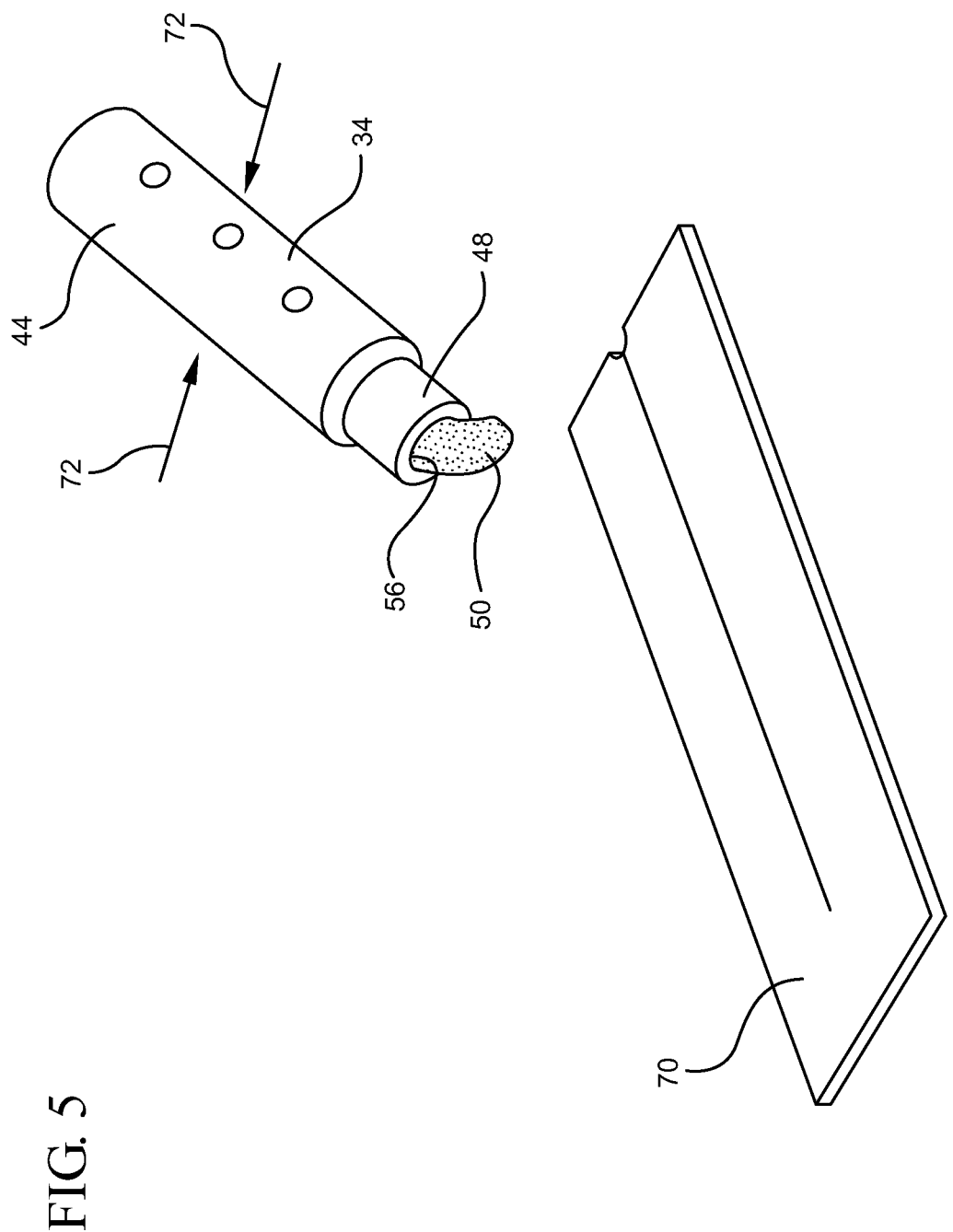
FIG. 5 illustrates a perspective view of a removable flash chamber dispensing a sample of blood on a blood test strip, according to some embodiments.

Reference will now be made to FIG. 5, which depicts the flash chamber 34 dispensing blood 50 onto a blood test strip 70. The test strip 70 can be used to test for glucose, creatine, cystatin C test, or other such test at the point of care, the location of the patient. Such diagnosis can provide rapid diagnostic results at the point of care, without the need to withdraw a blood 50 sample via a syringe, vacuum tube, or other traditional device. In some instances, the blood 50 can be dispensed into a diagnostic test device that performs diagnostic testing on the blood. In other instances, the blood 50 can be dispensed from the flash chamber 34 into a sterile vial or tube, such as a in-vitro test tube that is taken to a medical laboratory for testing.

The chamber body 44 of the flash chamber 34 can have various embodiments that can facilitate the dispensing blood 50 from the flash chamber 34. In some embodiments, at least a portion of the chamber body 44 is compressible to at least a small degree. When compressed, such as in an inward direction 72, the internal volume of the internal cavity 66 of the flash chamber 34 decreases, increasing the internal pressure of the internal cavity 66, and dispensing a sample of blood 50 from the distal opening 56. In some embodiments, the flash chamber 34 is rigid or semi-rigid. In some embodiments, only a portion of the flash chamber 34 is compressible. The compressible portion can be located and designed so that it does not compress during normal removal of the flash chamber 34 from the needle hub 36. In other embodiments, the chamber body 44 of the flash chamber 34 is a breakable ampoule, which when broken, dispenses blood 50 therefrom. In some embodiments, the distal opening 56 of the flash chamber 34 is shaped and sized so that a clinician can wick blood 50 therefrom using a test strip 70 or other device.

Reference will now be made to FIG. 6, which depicts another embodiment of a connection between the needle hub 36 and the flash chamber 34. As shown, in some embodiments, the needle hub 36 includes a valve 80 that can prevent blood 50 from spilling out of the proximal opening 60 of the inner bore 62 of the needle hub 36 when the flash chamber 34 is removed therefrom. In some configurations, the valve 80 is flexible and selectively opens upon insertion of the flash chamber 34 therein. In some embodiments, the valve 80 is made of an elastomeric material, such as silicon rubber or the like. The valve 80 can selectively close and seal when the flash chamber 34 is removed therefrom. The valve 80 can provide a fluid tight connection between the flash chamber 34 and the valve 80 when the flash chamber 34 is inserted therein. As shown, in some embodiments, the flash chamber 34 can coupled directly into the valve 80 with a press fit connection. As further shown, in some embodiments, the flash chamber 34 is not coupled to, nor does it contact, the introducer needle 30.

As shown, in some embodiments, the valve 80 includes a connection portion 90 that is coupled to the inner surface of the needle hub 36 and a barrier portion 82. The barrier portion 82 spans a cross section of inner bore 62 to seal the inner bore 62 upon removal of the flash chamber 34. The barrier portion 82 can include a hole or slit that selectively open and closes. The slit can be a straight slit, a Y-shaped slit, or a cross-shaped slit. The barrier portion 82 can also include an inward facing duckbill shape that at least partially can prevent the slit from opening in response to proximally oriented internal pressure on the valve 80. The valve 80 can retain the flash chamber 34 within the needle hub 36 until a threshold force is applied proximally 63 on the flash chamber. In some embodiments, the flash chamber 34 is retained in the needle hub 36 with a breakable connection 92, which breaks when a threshold force is applied proximally 63 on the flash chamber 34. The breakable connection 92 can be made of a breakable material. The breakable connection 92 can also have a scored line 94 and/or a stress riser that facilitates breaking at that point.

Referring still to FIG. 6, in some embodiments, the needle hub 36 includes a latch member 86 that extends distally from the needle hub 36. The latch member 86 permits the needle hub 36 to be is drawn proximally 62 and distally within the safety barrel 40 until the latch member 86 is drawn proximally passed an inward ridge 84. The inward ridge 84 can have a steep proximal face 92 that restricts the latch member's 86 distal movement. As such, the latch member 86 and the inward ridge 84 can prevent the needle hub 34 from advancing the introducer needle 30 out the safety barrel 40. The shape and configuration of the latch member 86 and the inward ridge can be adjusted, anticipated, and/or changed. Furthermore, other such means for limiting the needle hub's 36 distal movement can be incorporated into the needle assembly 22.

Figure 9:
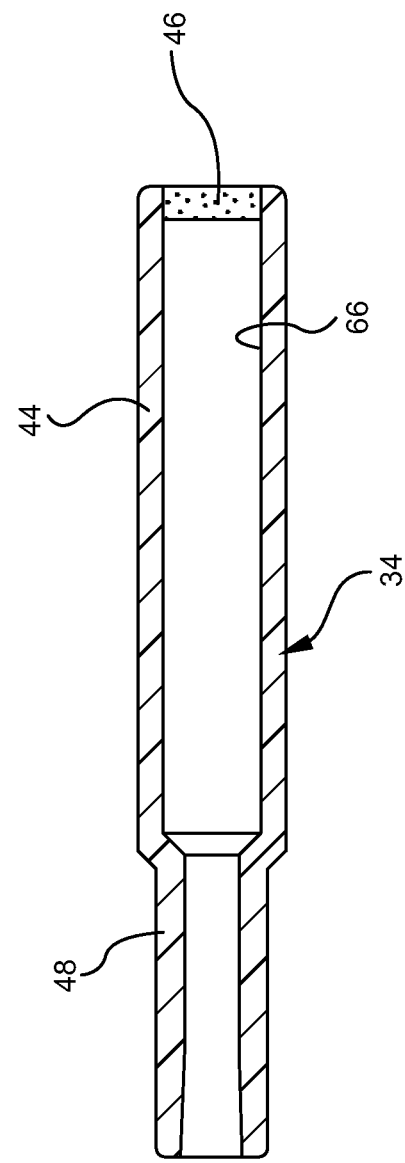
FIG. 9 illustrates a cross-section view of a removable flash chamber, according to some embodiments.

FIG. 9 depicts another embodiment of a flash chamber 34 that can be used with the valve 80 and needle hub 36 of FIG. 6. This flash chamber 34 includes a distal connector portion 48 that includes a narrow nose extension 130. The narrow nose extension 130 can pierce through the valve 80 and allows for effective resealing of the valve 80 after the removal of the flash chamber 34.

Figure 7:
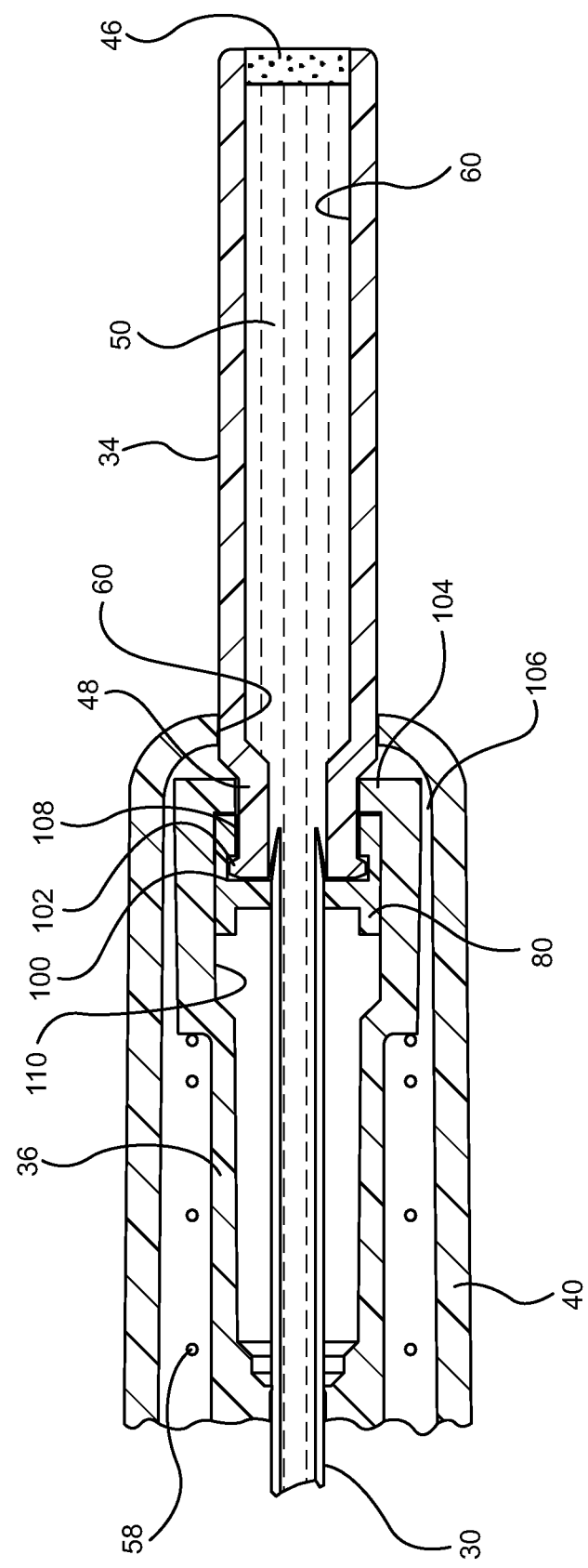
FIG. 7 illustrates a cross-section view of a proximal portion of another catheter assembly with a removable flash chamber, according to some embodiments.

Reference will now be made to FIG. 7, which depicts yet another embodiment of a connection between the needle hub 36 and the flash chamber 34. As shown, flash chamber 34 is removably coupled to the needle hub 36. The distal connector portion 48 of the flash chamber 34 includes an annular flange 102 that extends outwardly from the flash chamber 34. This distal connector portion 48 is positioned within proximal portion of the inner bore 62 of the needle hub 36. A valve 80 is located within this proximal portion of the inner bore 62. The valve 80 includes an inner cavity 108 that receives the distal connector portion 48 therein. The annular flange 102 of the distal connector portion 48 is interlocked within an inner groove 100 of the valve 80. The valve 80 is disposed within a distal region 110 of the inner cavity 108. The valve 80 and/or the flash chamber 34 can longitudinally within this distal region 110. This distal region is terminated at its distal end with an inward flange 104 of the needle hub 36. This inward flange 104 prevents the annular flange 102 of the flash chamber 34 from being withdrawn from the needle hub 36 until a threshold force is applied to the flash chamber 34. When a threshold force pulls the flash chamber 34, the proximal movement of the annular flange 102 forces the valve 80 and the inward flange 104 to flex outwardly into the space 106 between the needle hub 36 and the safety barrel 40. The characteristics, shapes, dimensions, and properties of the needle hub 36 and the valve 80 can be designed to require a certain threshold force that will allow a user to easily remove the flash chamber 34, while preventing the flash chamber 34 from falling out when it is slightly jarred, bumped, or touched.

In other embodiments, the flash chamber 34 is screwed onto the needle hub 36. As shown, the annular flange 102 can be angled to form one or more male threaded connectors and the inner groove 100 of the valve 80 and/or the inward flange 104 of the needle hub 36 can form a female threaded connector. Thus configured, the flash chamber 34 can be screwed into the needle hub 36. To remove the flash chamber 34 it can be unscrewed from the needle hub 36.

As shown in FIG. 8, in some embodiments, the flash chamber 34 is connected to the needle hub 36 via a keyed connection. The distal connector portion 48 can include a one or more keyed connector components 120 that mates with keyed connector components 122 in the proximal opening 60 of the safety barrel 40 and/or the needle hub 36. For example, in some instances, the keyed distal connector portion 48 is inserted into the keyed safety barrel 40 and/or the needle hub 36 in a distal direction 124. When fully inserted, the flash chamber 34 can be rotated, for example in a clockwise direction 126, to lock it in place. To remove the flash chamber 34, the clinician rotates the flash chamber 34 in a counter-clockwise direction and withdraws the flash chamber 34 in the proximal direction 63. In addition to the connections between the flash chamber 34 and the needle hub 36 described herein, other such connecting means for connecting the flash chamber 34 to the needle hub 36 can be incorporated into the catheter assembly 20.

From the foregoing, it will be seen that the present devices and methods efficiently collect a blood sample from a flash chamber that is removably coupled to the proximal end of an introducer needle. Since blood is already collected in this chamber, the use of this blood can avoid the need for a separate blood sampling procedure. Once removed, blood can be dispensed from the flash chamber into a point-of care diagnostic device, for rapid, prompt test results, which can enable time-sensitive health information, such as the risk of diabetes or impaired kidney function to be more quickly and easily acquired. Furthermore, the flash chamber can be sized for accommodate the needed blood sample. As such, the flash chamber can be enlarged, which increases the flashback visualization period.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly comprising:
a catheter hub;
an introducer needle having a lumen extending therethrough;
a needle hub coupled to a proximal end of the introducer needle, the needle hub forming an internal chamber having a proximal opening;
a flash chamber having a distal end that is positioned within the internal chamber and is removably coupled to the needle hub, an interior of the flash chamber being in fluid communication with the lumen of the introducer needle when the flash chamber is coupled to the needle hub; and
a safety barrel removably coupled to the catheter hub, the safety barrel being configured to capture a sharpened distal tip of the introducer needle when the needle hub is withdrawn proximally within the safety barrel, a proximal end of the flash chamber being positioned within the safety barrel prior to the needle hub being withdrawn proximally within the safety barrel, the safety barrel having a proximal opening configured to allow the flash chamber to extend proximally out through the safety barrel when the sharpened distal tip is captured within the safety barrel thereby allowing the flash chamber to be decoupled from the needle hub, the proximal opening being sized to prevent the needle hub from extending through the proximal opening.

2. The catheter assembly of claim 1, wherein the flash chamber comprises:
a chamber body defining an internal cavity; and
an air permeable membrane coupled to the chamber body and in fluid communication with the internal cavity.

3. The catheter assembly of claim 2, wherein the internal cavity of the chamber body of the flash chamber has an internal volume between about 0.1 mL to about 10 mL.

4. The catheter assembly of claim 1, wherein the flash chamber is press fit into one or both of the needle hub or introducer needle.

5. The catheter assembly of claim 1, wherein the flash chamber is screwed onto the needle hub.

6. The catheter assembly of claim 1, wherein the flash chamber is selectively coupled to the needle hub or the introducer needle via a keyed connection.

7. The catheter assembly of claim 1, wherein the flash chamber is selectively coupled to the needle hub or the introducer needle via a breakable connection.

8. The catheter assembly of claim 1, wherein the flash chamber is a breakable ampoule.

9. A catheter assembly comprising:
a catheter adapter; and
a needle assembly comprising:
an introducer needle having a lumen extending therethrough;
a needle hub coupled to a proximal end of the introducer needle, the needle hub forming an internal chamber having a proximal opening;
a flash chamber having a distal end that is positioned within the internal chamber and is selectively coupled to the needle hub or the introducer needle, an interior of the flash chamber being in fluid communication with the lumen of the introducer needle when the flash chamber is coupled to the needle hub; and
a safety barrel removably coupled to the catheter hub, the safety barrel being configured to capture a sharpened distal tip of the introducer needle when the needle hub is withdrawn proximally within the safety barrel, a proximal end of the flash chamber being positioned within the safety barrel prior to the needle hub being withdrawn proximally within the safety barrel, the safety barrel having a proximal opening configured to allow the flash chamber to extend proximally out through the safety barrel when the sharpened distal tip is captured within the safety barrel thereby allowing the flash chamber to be decoupled from the needle hub, the proximal opening being sized to prevent the needle hub from extending through the proximal opening.

10. The catheter assembly of claim 9, wherein the needle hub comprises a valve through which the flash chamber extends, the valve sealing the proximal opening of the needle hub when the flash chamber is decoupled from the needle hub.

11. The catheter assembly of claim 10, wherein the flash chamber is selectively coupled to the valve.

12. The catheter assembly of claim 9, wherein the flash chamber is selectively coupled to the needle hub and the introducer needle.

13. The catheter assembly of claim 9, wherein the flash chamber is screwed onto the needle hub.

14. The catheter assembly of claim 9, wherein the flash chamber is selectively coupled to the needle hub or the introducer needle via a breakable connection, the breakable connection including at least one scored line and a stress riser.

15. The catheter assembly of claim 9, wherein the flash chamber is a breakable ampoule.

16. A catheter assembly comprising:
a catheter adapter from which a catheter extends distally;
a safety barrel secured to a proximal end of the catheter adapter, the safety barrel having a proximal opening;
a needle hub contained within the safety barrel, the needle hub including an introducer needle that extends distally from the needle hub within the catheter when the needle hub is in a first position, the needle hub forming an internal chamber having a proximal opening;
a flash chamber having a distal end that is positioned within the internal chamber and that is secured to a proximal end of the needle hub, the flash chamber being in fluid communication with the introducer needle, the flash chamber being removable from the needle hub, a proximal end of the flash chamber being positioned within the safety barrel when the needle hub is in the first position;
wherein the needle hub is configured to move proximally within the safety barrel to a second position to withdraw the introducer needle into the safety barrel, the proximal movement causing the flash chamber to move proximally through the proximal opening of the safety barrel thereby allowing the flash chamber to be decoupled from the needle hub and removed from within the safety barrel while the needle hub remains within the safety barrel, the proximal opening being sized to prevent the needle hub from extending through the proximal opening.

17. The catheter assembly of claim 16, wherein the flash chamber collects blood that flows through the introducer needle and into the flash chamber while the flash chamber is secured to the needle hub, the flash chamber being compressible to reduce its internal volume thereby allowing the collected blood to be ejected from the flash chamber.

18. The catheter assembly of claim 16, wherein the safety barrel is removable from the catheter adapter after the introducer needle is withdrawn into the safety barrel.

19. The catheter assembly of claim 16, further comprising:
a spring positioned between a proximal portion of the needle hub and a distal portion of the safety barrel, the spring being compressed when the needle hub is in the first position, the decompression of the spring causing the proximal movement of the needle hub.

* * * * *